United States Patent [19]
Giannone

[11] Patent Number: 6,094,998
[45] Date of Patent: Aug. 1, 2000

[54] PORTABLE SAMPLE SYSTEM AND METHOD FOR FILLING A PORTABLE SAMPLE CONTAINER

[75] Inventor: Frank S. Giannone, North Bellmore, N.Y.

[73] Assignee: MMC International Corp., Inwood, N.Y.

[21] Appl. No.: 09/194,771

[22] PCT Filed: May 30, 1997

[86] PCT No.: PCT/US97/09602

§ 371 Date: Dec. 2, 1998

§ 102(e) Date: Dec. 2, 1998

[87] PCT Pub. No.: WO97/46861

PCT Pub. Date: Dec. 11, 1997

Related U.S. Application Data

[63] Continuation of application No. 08/658,316, Jun. 5, 1996, Pat. No. 5,691,488.

[51] Int. Cl.[7] ................................................. G01N 1/12
[52] U.S. Cl. ................................................. 73/863.86
[58] Field of Search .......................... 73/863.86, 863.82, 73/864.31, 864, 63, 864.24, 864.25, 863.85; 33/717, 718

[56] References Cited

U.S. PATENT DOCUMENTS

| 3,505,820 | 4/1970 | Draper et al. ..................... 73/864.31 X |
| 5,165,246 | 11/1992 | Cipolla et al. ........................... 62/47.1 |
| 5,408,889 | 4/1995 | Parault ............................. 73/864.31 X |
| 5,408,890 | 4/1995 | Klaus ................................ 73/863.86 X |
| 5,452,620 | 9/1995 | Giannone ............................. 73/864.31 |
| 5,460,973 | 10/1995 | Schrader .................................. 436/167 |

*Primary Examiner*—Thomas P. Noland
*Attorney, Agent, or Firm*—McAuley Nissen Goldberg & Kiel, LLP

[57] ABSTRACT

A portable sampling system (10) and method for use with a cargo tank's vapor control valve (12) or other entry device to enable an operator to extract and bottle a product sample in place without transfer of a collected sample to another container or through an open atmosphere. A built-in sampling valve (34) and sample bottle fill attachment (44) are coupled with a vapor return hose assembly (58) to a hand held gauging apparatus for collection of the product sample free of human contact and so as to eliminate vapor release to the atmosphere and to protect an end user from possible exposure to toxic vapors. A tape reel mechanism (14) is connected with a sampling barrel (32) through which a product sampling tube (33) attached to a tape reel (66) in tape reel housing (16) and is lowered into the tank (12a) to obtain the product sample. A vapor control valve (12) is coupled between the sampling barrel and the tank.

21 Claims, 6 Drawing Sheets

PORTABLE SAMPLE SYSTEM AND METHOD FOR FILLING A PORTABLE SAMPLE CONTAINER

CROSS REFERENCE TO RELATED APPLICATIONS

This application is the U.S. national stage application of international application Ser. No. PCT/US97/09602, filed May 30, 1997 and published as WO 07/46861 on Dec. 11, 1997 which is a con of U.S. patent application Ser. No. 08/658,316, filed Jun. 5, 1996, which issued as U.S. Pat. No. 5,691,488 on Nov. 25, 1997 and for which benefits under 35 U.S.C. 120 are claimed.

TECHNICAL FIELD

This invention is concerned with a closed portable sampling apparatus, and a sampling system and method for obtaining a sample of a liquid product which may be hazardous. More particularly, the invention is concerned with gauging and sampling of liquid bulk petroleum and chemical products.

BACKGROUND

The Restricted gauging units are of a design that they are open to the atmosphere, therefore allowing such vapor to escape, and require hand dumping of a collected sample.

DISCLOSURE OF THE INVENTION

The closed portable sampling system which forms the subject matter of this application is an improvement over prior art restricted systems and gauging units. The invention is concerned with a vapor return hose assembly and a vapor return hose connection, a sampling barrel with a built-in sampling valve and a flow control valve forming part of a bottle fill attachment which upon opening, any interior positive pressure assists in pushing the extracted sample into a sample container.

One of the features of the present invention is the use of an integrated sampling diverter valve which operates in conjunction with but independently of a cargo tank's existing vapor control valve. An important feature of this invention is that once the apparatus of the invention is attached to the tank or a storage container, by an entry valve or adapter fitting, an operator can use the apparatus forming part of the system and perform the method of the invention both to extract and to bottle a product sample in place without transfer of the collected sample to another container, thereby using the same container for collection and bottling and avoiding any slight possible emission to the atmosphere.

The closed sampling apparatus according to the teachings of this invention includes the vapor return hose assembly, the vapor return hose connection connected to the sampling tape's wiper assembly and comprises a vapor return check valve and the vapor return hose forming part of the vapor return hose assembly which has one end coupled to the vapor return check valve connection and the other end coupled with the sampling container or bottle.

The system of the present invention includes an integrated sampling diverter valve which operates in conjunction with but independently of a product tank's existing entry valve. The apparatus which can be attached to any entry valve associated with the product tank is used in conjunction with a sampling valve which forms the subject matter of U.S. Pat. No. 5,452,620 granted on Sep. 20, 1995 in the name of the inventor of the subject matter of this application and assigned to the assignee of this application. An operator can then extract and bottle a product sample in place without the necessity of transferring the collected sample to another container.

The closed unit according to the invention eliminates vapor release, and thereby also protects the end user from possible exposure to potentially toxic vapors.

DETAILED DESCRIPTION OF THE BEST MODE

Figures 1, 1A, 1B:
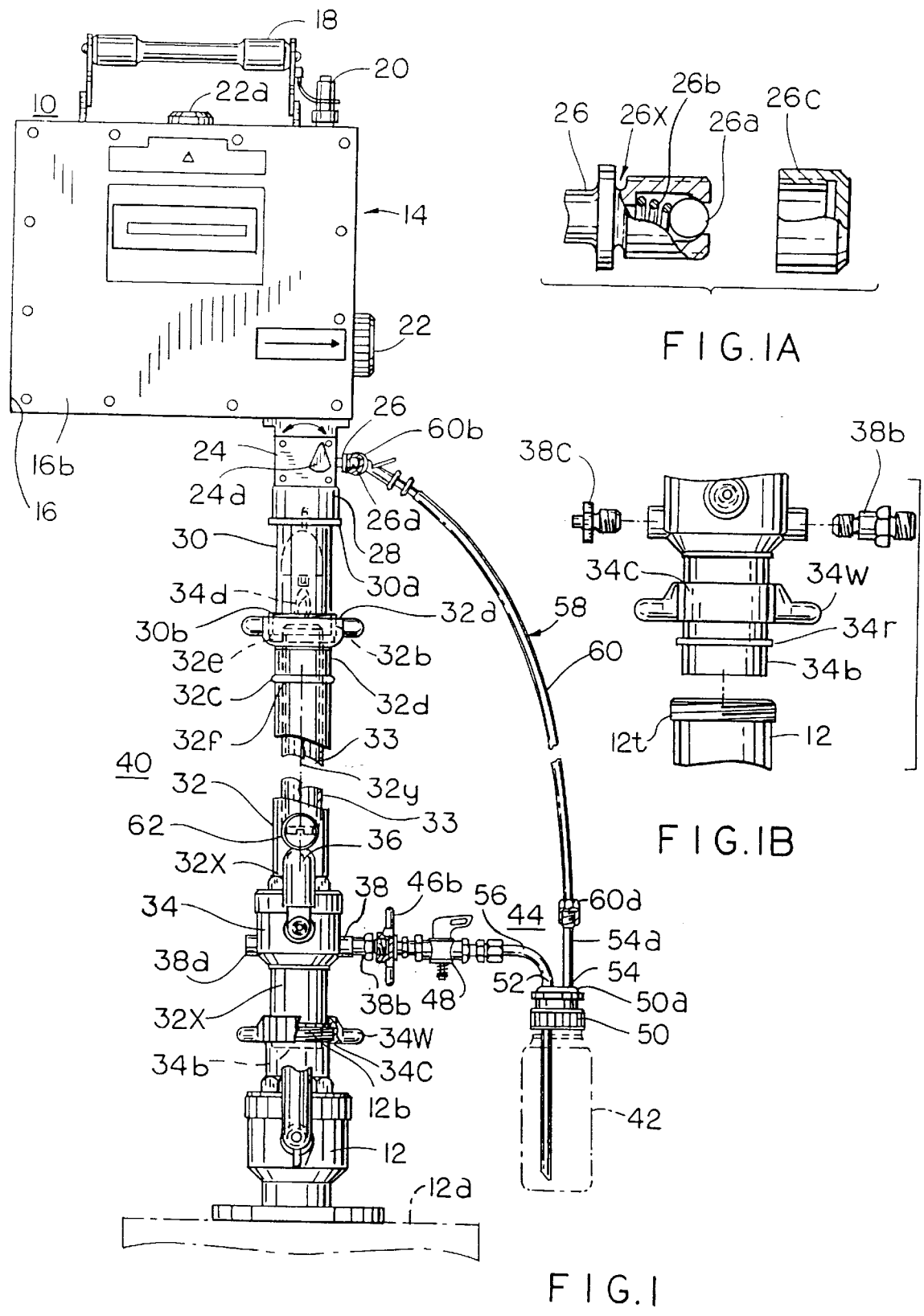
FIG. 1 is a schematic front view of an apparatus for use in connection with the self-contained sampling system according to the invention with the sampling barrel shown in one particular orientation thereof and having a window to view the bottom of a product sampling tube contained within the sampling barrel and of the sampling valve.
FIG. 1A is a detail of an internal spring loaded vapor return check valve.
FIG. 1B is a detail of FIG. 1 showing a connection to a cargo container vapor valve or other pipe-like adapter.
Figure 7:
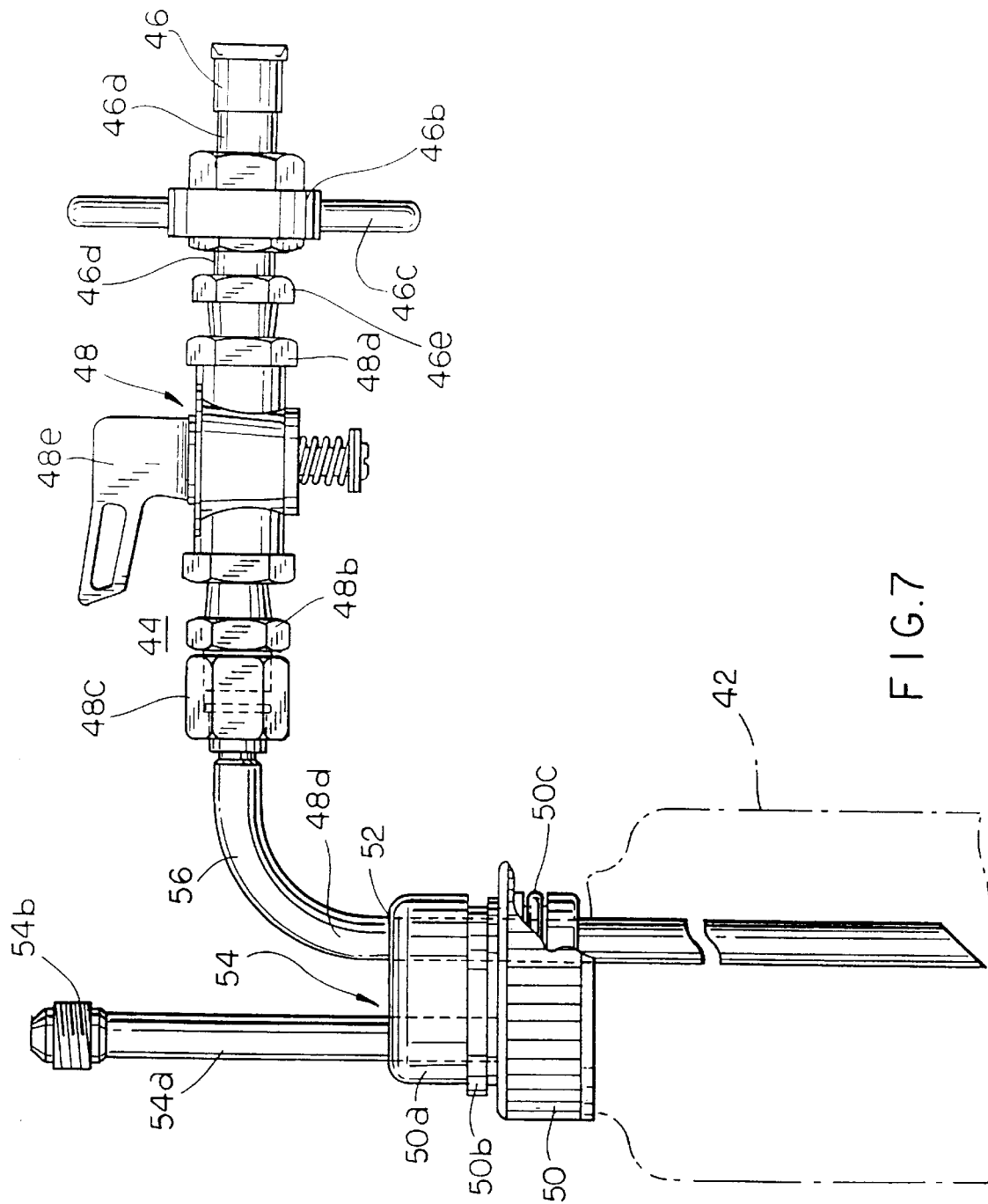
FIG. 7 is a detail of the sample fill and flow control apparatus which is attached between a sample valve drain port connector and a fill bottle or container for sample collection, and upon removal, capped for later laboratory analysis.

Referring to FIG. 1, which shows apparatus 10 for use in direct connection with a conventional existing standard vapor control valve 12 or other equivalent or tank appendage valve, which can be connected to apparatus 10 by means of a suitable adapter, and thereby attached to a cargo or tank container 12a, schematically shown, containing a liquid from which a sample is to be withdrawn and transferred to sample bottle or container 42 through bottle fill attachment assembly 44 (the entire assembly being shown in FIG. 7).

Figure 4:
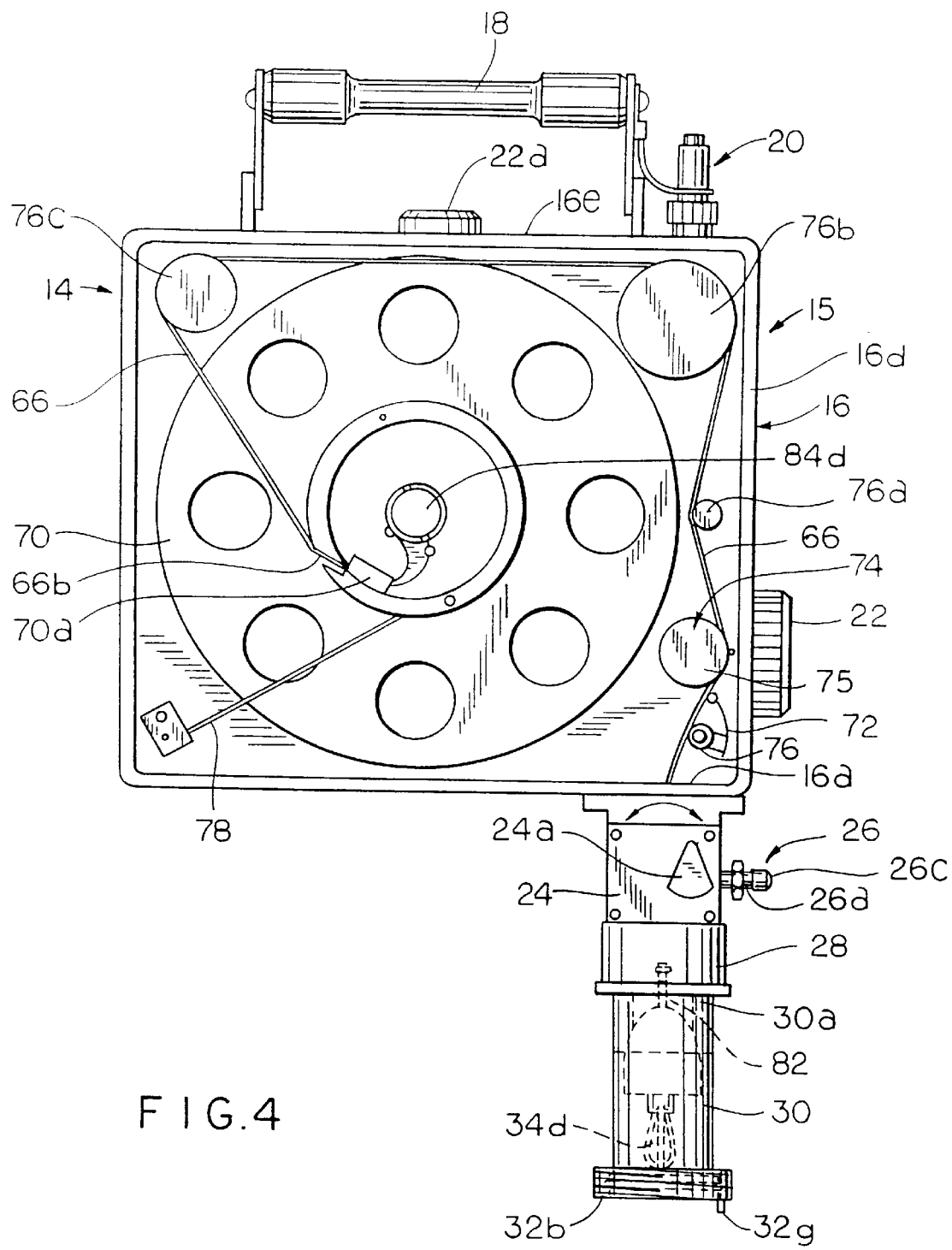
FIG. 4 is an open view of the interior of the casing of the apparatus with the cover removed to show the internal parts and portions thereof coupling the tape reel casing or housing to the sampling barrel.

Apparatus 10 includes a completely enclosed tape and reel mechanism 14 in a casing or reel housing 16 with its exterior cover in place for housing sampling tape and reel mechanism 15 with its exterior cover removed (see FIG. 4). Casing or reel housing 16 is provided with a swing away carrying handle 18 and is pivotally connected to casing or housing 16 for hand carrying the apparatus. A pressure/vacuum valve push button 20 is connected with the top of casing 16 for easy access thereto and for purposes as explained hereinafter. Housing 16 includes at least one sight or view port 22, forming a primary view port, which is preferably provided on the side of the casing 16 and desirably a second view port 22a, forming a secondary view port for tape motion direction is provided under handle 18.

An anti-static treated gauging tape 66, see FIG. 4 is contained and enclosed in casing or housing 16, and the viewing ports 22 and 22a provide the operator with an immediate sense as to whether the unit including tape 66 (FIG. 4) and attached product sampling tube 33 is being raised or lowered. A single viewing port 22 is satisfactory, but, it is easier for the operator to ascertain direction of tape and product sampling tube movement when two viewing ports are used. A fully re-wind tape reading label is posted just below each sight or viewing port indicating the correct tape reading at the fully rewound position, which is mechanically set by an internal tape-head stop-bushing 82 (see FIG. 4) located within the barrel piece attached to the tape wiper housing. The operator can visually view the gauge tape reading to confirm full re-wind condition, before closing the associated vapor control valve or sampling valve 34. This condition is visually determined by sighting the bottom of product sampling tube 33 through viewing port 62 located at the lower end of sampling barrel tubular assembly 32, prior to releasing the collected product sample.

Tape and reel mechanism 14 includes a member forming a tape wiper housing cover and wiper component mounting plate 24 for housing a tape wiper assembly and tape wiper actuating knob 24a projecting from and attached to the bottom 16b of casing 16. Member 24 is directly coupled with the base or bottom 16b and also provides for a vapor return check valve fitting 26 to member 24, for connection to a vapor return hose with quick connection end.

Port 22 can be used for tape payout determination without reference to an established gauging platform reference point. When used as such, a gauging platform reference may be applied to the tape reading for zero level reference correction. Tape wiper actuation knob 24a is provided on member 24.

A dual purpose winding crank or crank handle 84 (see FIG. 5) is provided. At the completion of a tape payout or rewind operation, the winding crank can be repositioned to serve as a tape reel lock.

In a closed reel housing, anti-rotation arm 78 (see FIG. 4) is necessary because it would be possible without such anti-rotation arm to bottom out tape payout and then by continued reel turning, cause the tape to be rewound in the opposite direction causing false gauging tape readings, and possible tape fold damage, resulting in short gauging tape life.

Sample container 42 is connected with vapor return fitting 26 by vapor return and control hose assembly 58 which includes vapor return hose 60 having one end provided with connector 60a in the form of a thread nut connected to container 42 and its other end provided with quick connector 60b, for gasket sealed connection to vapor return check valve fitting 26, which houses a spring loaded vapor return check valve 26x including ball 26a and spring 26b. Fitting 26 is externally threaded to receive quick connector and vapor return check valve depressor 60b for depressing ball 26a and spring 26b, or cap 26c as shown in FIGS. 1A and 4. Quick connector 60b contains a pin depressor for pushing back the sealing ball 26a of spring loaded vapor return check valve 26x, thereby allowing returning vapor communication with the interior of casing 16.

Figure 6:
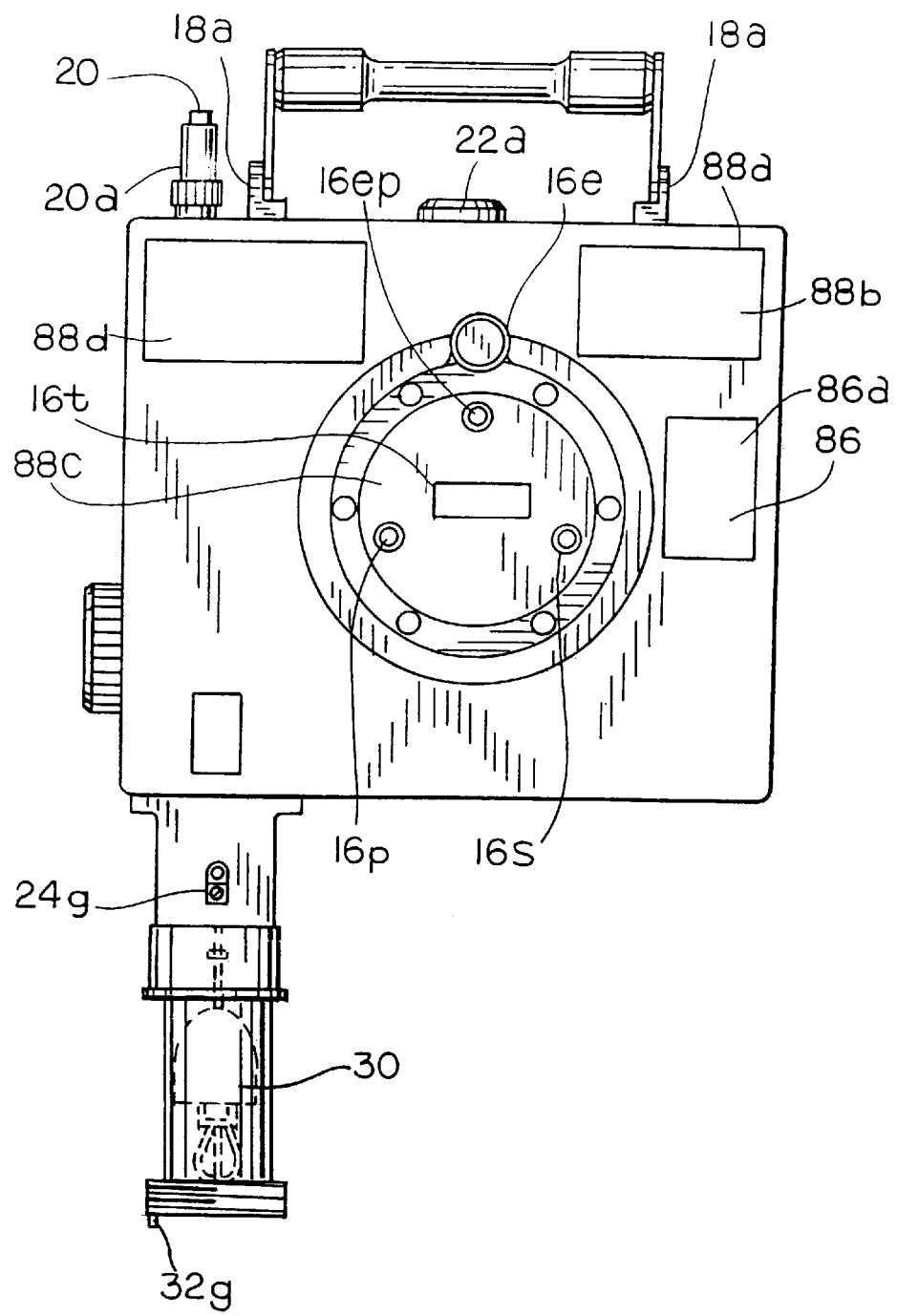
FIG. 6 is another view of the closed gauging unit shown in FIG. 5, showing a rear side thereof opposite to the side shown in FIG. 1, and showing the tape reel winding handle, which also serves as a tape reel positive lock mechanism.

As a safety precaution, the apparatus is provided with a conventional grounding cable and lug 24g, see FIG. 6 which should be connected to a known good hull and vessel ground for grounding the entire apparatus 10. Connector 28 at the bottom of member 24 including the tape wiper housing is provided for connection to stub barrel connector 30 for coupling thereto of an outer tubular member forming sampling barrel tubular assembly 32 for enclosing product sampling tube 33. Stub barrel wiper housing connector 30 has one end 30a connected and sealed with connector 28 connected to member 24 and its other end, having an externally threaded lower stub barrel end 30b connected with sampling barrel 32 by upper coupler nut 32a. Sampling valve 34 includes an internal valve member through which internal product sampling tube 33 passes.

Product sampling tube 33 has its upper end connected with a free end of the gauging tape 66 (FIG. 4) and its lower end and passes through sampling valve 34 to enter the cargo or tank container 12a. Valve 34 is connected with built-in sampling valve handle 36 for opening and closing the internal valve member thereof and is shown in its open position with built-in sampling valve handle 36 in its vertical position. Handle 36 is axially aligned when valve 34 is open with the longitudinal axis 32y of the hollow inner tube portion of sampling barrel 32 through which product sampling tube 33 is raised and lowered. Valve 34 also functions as a vapor control valve at its position proximate to cargo container 12a. The details of the novel sampling valve are shown as a separate unit in U.S. Pat. No. 5,452,620.

Sampling valve 34 includes at least one outlet drain port 38 for connection to sample container 42 (see FIG. 2) by fill attachment assembly 44.

Referring to FIG. 7, connector 46 forms part of fill attachment assembly 44 for coupling and uncoupling fill attachment assembly 44 to and from primary drain port 38. Connector 46 includes sleeve tube connector 46a and a pair of wing extensions 46c on eared coupling unit 46b for rotation thereof for coupling and uncoupling fill attachment assembly 44 to and from outlet drain port 38.

Outlet port 38a (see FIG. 1) is another or optional port substantially similar to drain port 38 and provided with cap closure or pipe plug 38c (see FIG. 1B). Ports 38 and 38a are threaded for primary connection of connector adapter or drain port fitting 38b with inner threaded portion of sleeve tube connector 46a. Port 38a diametrically opposite to and preferably aligned with drain port 38 is a clean out port, and facilitates cleaning of sampling valve 34. Drain port fittings 38 and 38a of the sampling valve may be covered with a threaded seal cap 38c which are removable before attaching sampling bottle fill attachment assembly 44 to port 38 or port 38a.

Figure 2:
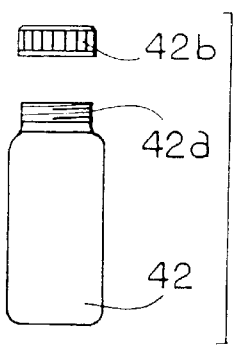
FIG. 2 is a separate view of a sample container or bottle shown in FIG. 1 together with a cap sealing closure for closure of the sample container or bottle.

Sample flow control valve 48 controls the flow of liquid from sampling barrel 32, after being released, into sample bottle 42 as shown in detail in FIG. 7. Bottle 42 as shown in FIG. 2 is provided with an outer threaded portion or threaded opening end 42a, for mating and sealing engagement with sampling bottle closure cap 42b having inner sealing threads 42c which mate with outer threads 42a. Threads 42a together with an elastomeric seal 42d provide a tight sealing engagement for sealing the contents after a sample is placed into sample bottle 42.

Sampling bottle 42 is provided with a separate cap closure such as seal plug or securing cap 50 cooperates with fill assembly 44 to transfer a sample from product sampling tube 33 to sample bottle 42, and has entrance way 52 for use to supply a sample and exit way 54 for the return of product vapor to the interior of apparatus 10 by vapor return hose 60. Flow control valve 48 has outlet pipe 56 connected with entrance way 52, and exit way 54 is connected to vapor return check valve fitting 26 through vapor return hose assembly 58, vapor control hose 60 connector 60a for connection to exit way 54 through connector extension 54a for vapor return tube by fitting 54b, then extending therefrom and quick connector 60b for connection to vapor return check valve fitting 26.

Bottle fill attachment may be connected to sampling valve 34, before or after connecting the sample system to a vapor control valve. As a safety precaution, before connecting the sampling system to vapor return check valve 26, insure that flow control valve 48 is in its full closed position.

At the end of sampling barrel 32 coupled to sampling valve 34, sampling barrel 32 is provided with a window forming part of viewing port 62 for viewing the interior of sampling barrel 32 at its indicated location, and as shown in FIG. 1, the bottom of movable built-in product sampling tube 33 is viewed, also see FIGS. 3A to 3E. Viewing port 62 permits viewing of the product sampling tube 33 and dumped product sample.

Referring to FIG. 1A, at a lower end of sampling valve 34, male tubular guide portion 34b is provided for easy entry into female top threaded portion 12b of an existing vapor control externally threaded vapor control valve 12 or similar tank entry device, lower connector coupler 34c in the form of a nut or collar has a pair of extending turning wings 34w and is provided to couple and decouple coupling portions 12b and 34c to and from each other, respectively. Connector 34 is also provided with an internally threaded portion threaded complementary to outer threaded portion 12t to facilitate rapid connection and disconnection. Tubular guide portion 34b is provided with a stop ring 34r to control the depth of guide portion 34b as it moves into the interior of the standard vapor control valve 12.

Figure 3A:
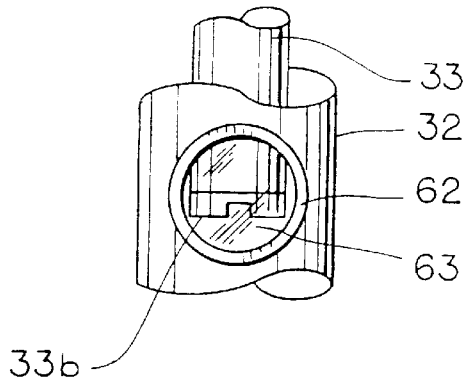
FIG. 3A is a partially detailed enlarged view of the sampling barrel and the bottom of the product sampling tube shown in its full stow or retracted position.
Figure 3B:
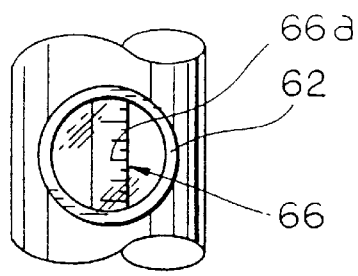
FIG. 3B is a view similar to that of FIG. 3A showing the partially detailed enlarged view of the sampling barrel and a gauging tape contained within the sampling barrel and attached to the product sampling tube with the gauging tape payout and a display of the payout distance to product surface level at the window port above the sampler valve at approximately six inches above the top of the vapor control valve as shown in FIG. 1.
Figure 3C:
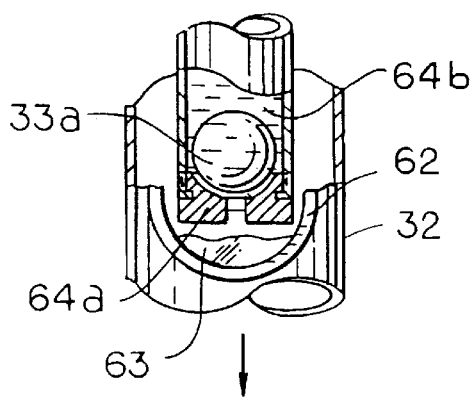
FIG. 3C is a view generally similar to that of FIG. 3A, but with the product sampling tube raised for viewing through the window and showing the product sampling tube having a portion cut away illustrating the product sampling tube ball check valve containing a sample with the tape raised to its full stow mark in the tape reel.

Referring to FIGS. 3A to 3E, and in particular to FIGS. 3A and 3C which show the bottom of product sampling tube 33 having a lower end portion which is a ball check valve assembly 64, and a portion of the sampling barrel 32. Sampling barrel 32 near the lower end thereof is provided with viewing port 62 and preferably a second viewing port 62a, preferably diametrically opposite to each other for axial alignment therewith.

In FIG. 3A, product sampling tube 33 is shown in a first position thereof, and in FIG. 3B, product sampling tube 33 is lowered into cargo container 12a so that tape 66 is visible through window 62 or 62a. The FIG. 3A position is a fully rewound condition. Product sampling tube 33 in FIG. 3A is shown in its full stow position with the apparatus 10 attached to vapor control valve 12 which is opened for entry of product sampling tube 33 into cargo container 12a. Sampling valve 34 and vapor control valve 12 are both open so that product sampling tube 33 can be lowered to the desired ullage level in the cargo container. FIGS. 1 and 3A show product sampling tube 33 with the tape fully rewound.

FIG. 3A, indicates commencement of operation, and bottom 33b of the product sampling tube 33 is seen as it would appear with its associated gauging tape at its fully rewound and locked condition.

The position of the product sampling tube 33 as viewed through sight port 62 is preferably six inches above the top of the vapor control valve 12.

In the FIG. 3B position, the tape is shown in an unwound condition thereof in its condition with bottom or base 33b or bottom of sampling tube 33 in the cargo container 12a after it has been lowered for collection of a sample.

Figure 3D:
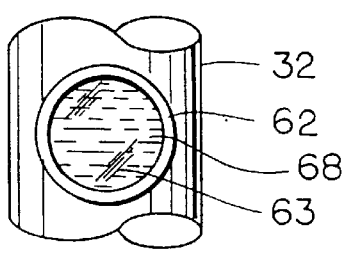
FIG. 3D is another view of the sampling barrel having a product sampling tube contained therein, but lowered to a position below the window and not visible with a sample of the liquid sample contained within the product sampling tube which was previously discharged upon leaving the product sampling tube after obtaining the sample and now the sample is contained in the area/volume within the sampling barrel for subsequent discharge through the sampling valve, via a sample bottle fill attachment (see FIG. 7) into a sample bottle (see FIGS. 1 and 2).

FIG. 3C shows product sampling tube 33 or bottom 33b after a sample has been collected and withdrawn, and product sampling tube 33 has a portion partially cut away at 64b, to show check valve ball 33a and liquid sample 68 contained therein. The filled product sampling tube 33, is shown returned to its full stow position. Gauging tape reel 70 should at this time be locked in place by means of reel drum handle lock 84b, and handle 84 is shown moved to its vertical position. The built-in sampling valve is then rotated to its closed position. FIG. 3D shows liquid sample 68 as viewed through window 62 after the release thereof from product sampling tube 33 into barrel 32 of sampling valve 34, and prior to discharge through bottle fill assembly 44 into container 42. Here the product is filling the view port window 62, after the product sampling tube 33 which is provided with a ball check valve to hold the sample in the product sampling tube 33 until released by a mechanism to raise the ball and have the sample discharge through sample valve 34, once the sampling tube has been lowered, and the internal check valve ball 67 of product sampling tube 33 is raised as described in U.S. Pat, No. 5,452,620. The sampling valve is a positive shut-off ball, valve, and handle 36 is rotatable through an angle of 90° to open and to close the ball valve.

After product sampling tube 33 has been slowly lowered into the cargo container to the desired ullage level, product sampling tube 33 is steadily raised to the full stow position of the tape in housing 16 to its full stow mark and the tape is locked to prevent any further movement thereof, and to the position shown in FIG. 3C. Sampling valve 34 is then closed sealing off any pressure from container 12a pressure.

Figure 3E:
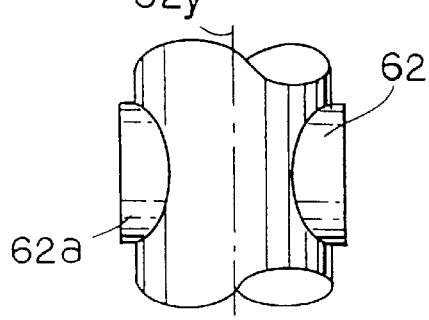
FIG. 3E is a modification of the sampling barrel shown in FIGS. 3A to 3D with an additional window.

FIG. 3E shows a partial view of tubular assembly sampling barrel 32 with port 62 on one side, and port 62a at about 180° displaced or diagonally opposite thereto to provide two in-line view ports. A single view port is usable, but, it is preferred to use two ports diagonally opposite to each other, to provide better lighting for viewing of the tape 66, and to provide an in-line view port arrangement.

The gauging tape viewing ports 62 and 62a are preferably covered with specially tempered glass elements covers 63. These tempered glass covers 63 are easily removed for cleaning or replacement purposes.

At times due to ambient temperature conditions, and interior product tank temperature differences, condensation may appear on the main housing view ports, but this does not interfere with this operation.

View ports 62, 62a on sampling barrel 32 are preferably situated approximately six (6) inches above the sampling barrel end connected to sampling valve 34. The center of the sampling barrel view ports 62, 62a are in line with the zero ullage preference plane.

Built-in sampling valve 34 is a sub-assembly which connects sampling barrel 32 to a fixed vapor control valve and is connector 34c which includes lower coupling nut or collar for connection to any fixed vapor control valve, such as a "B" series MMC made available by the assignee of this application.

Short stub barrel connector 30, attached to connector 28 containing the reel housing wiper assembly at stub barrel wiper housing connector end 30a, remains in place when sampling barrel tubular assembly 32 is removed for storage and product sampling tube 33 is detached from gauging tape 66.

Threaded joint 32b at the upper end of the sampling barrel tubular assembly 32 and stub barrel piece 30 are "O" ling sealed by O-ring 32c when threaded and joined together.

The location of thread joint of internally threaded coupling ring 32b has been chosen to allow easy snap hook assembly of product sampling tube 33 to the gauging tape by hook 34d, see FIGS. 1 and 4.

Figures 5, 5A:
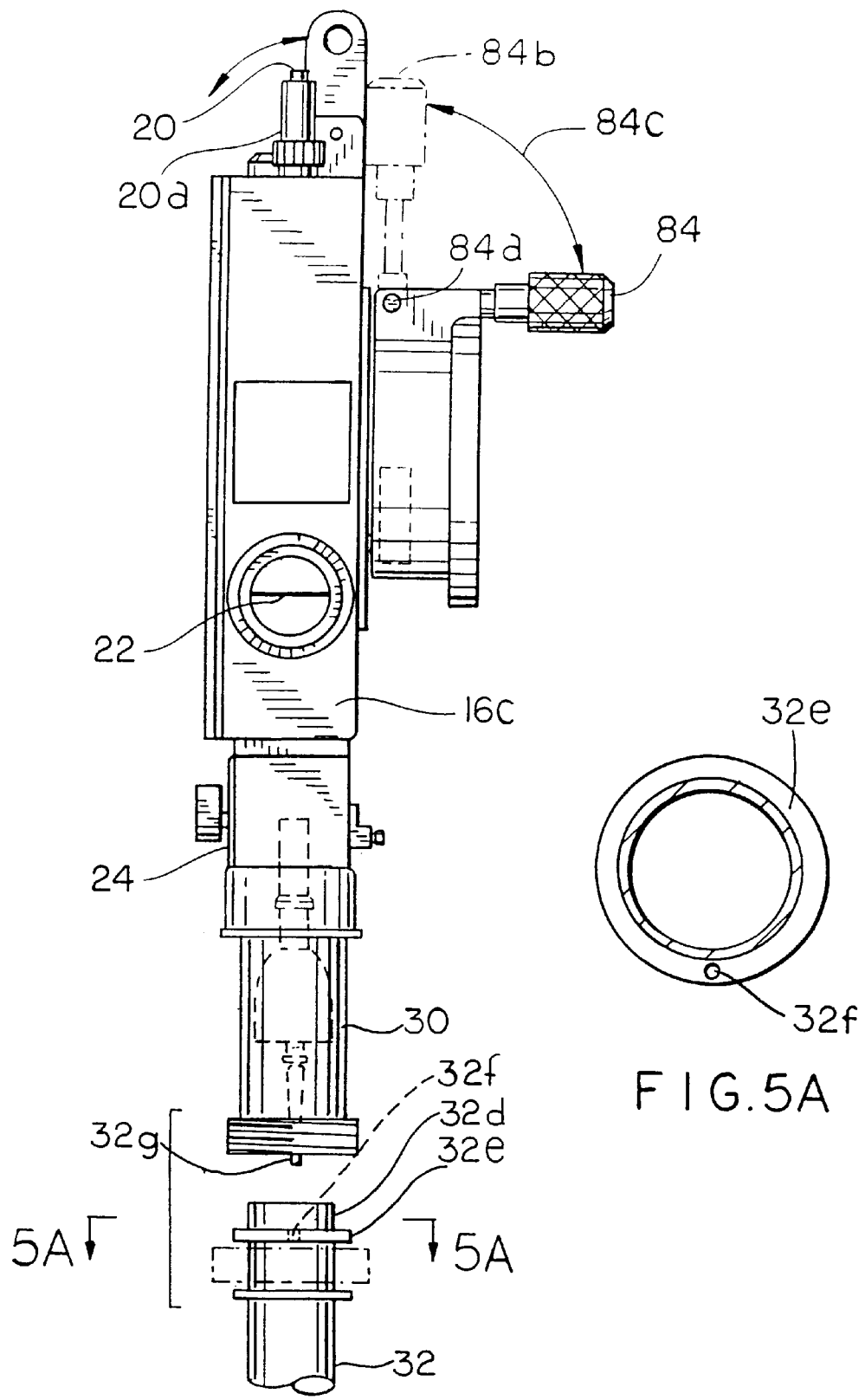
FIG. 5 is a schematic side view of the closed sampling unit showing a full view of an additional gauging tape viewing port on its narrow case side and also showing a section of a portion or partial modification of the sampling barrel.
FIG. 5A is a sectional view of the sampling barrel tubular assembly taken on line 5A—5A of FIG. 5 showing an alignment ring and pin alignment hole.

Referring to FIGS. 5 and 5A, top end 32d of sampling barrel tubular assembly 32 has fixed ring 32e with pin alignment hole 32f (see FIG. 5A) drilled in it, which is adapted to receive locator pin 32g extending from externally threaded stub barrel connector 30 for alignment of stub barrel connector 30. Fixed ring 32e prevents upper coupler nut 32a from sliding down barrel tubular assembly 32. FIG. 6 also shows locator pin 32g extending from stub barrel connector 30.

When sampling barrel tubular assembly 32 has been seated within stub barrel connector 30, internally threaded coupling ring 32b, attached to sampling barrel 32, is threaded to stub barrel piece 30, attachment is completed with the graduated tape face marking, properly aligned in the viewing port for reading purposes.

With gauging tape 66 substantially fully re-wound, (see FIG. 3C) bottom or base 33b of the product sampling tube may be seen through sampling barrel view port 62. Sampling barrel view port 62 or 62a also becomes another means of determining a substantially fully stowed tape.

Referring to FIG. 4 showing one side of casing or housing 16 removed to show interior portions and sampling tape and reel mechanism 15.

The interior of housing 16 contains inlet 16a to housing 16 schematically shown for tape 66. Positioned within housing 16 is reel 70 having molded epoxy tape end piece 70a, for the gauging tape and ground wire attachment, to which one end 66b of tape 66 is held. Tape 66 which enters housing 16 though inlet 16a passes over splash guard 72 and then passes over tape guide and cursor pin assembly 74, which includes cursor pin 75 schematically shown as a roller, and then around guide rollers 76 including idler roller 76a, tape guide rollers 76b and 76c for connection with the reel 70 by means of the tape end piece 70a. Anti-rotation spring-loaded arm 78 is coupled with reel 70 to prevent an unwanted payout of tape 66 and reel 70 and to stop reel motion when tape 66 is fully extended.

When the apparatus is used for sampling purposes, primary viewing port 22 on vertical side 16d (as conventionally hand held and as shown in the drawings) and second view port 22a located at the top 16e of the tape reel housing are normally used for viewing the approximate payout gauging tape 66 and its product sampling tube 33. These view ports are preferably physically located one foot or its metric equivalent apart from each other, as the tape moves along the tape path.

Secondary viewing port 22a also serves another important function which is to provide the operator with an immediate sense as to whether the tape and sampling tube 33 is being raised, lowered or rewind completed. This is particularly important for a closed system. This is not a trivial requirement, because the gauging tape 66 is effectively in a closed box or environment and the operator may at times lose the particular or actual sense of tape direction movement as the reel is in motion. The direction or tape movement measurement, other than through the windows, is not directly in view.

The filly re-wound stop position is mechanically set by an internal tape head stop bushing 82, located within stub barrel connector 30 which is attached to the tape wiper housing 24 by means of connector 28 to the stub barrel wiper housing connector end 30a.

Winding crank 84 is shown in full outline in FIG. 5, and it is pivotable about pivot 84a to its fully stowed position with the handle shown at 84b in dashed outline juxtaposed to the side of housing 16 when not used for winding and in its locked condition. At the completion of either a tape payout or re-wind operation, the winding crank is re-positioned in the vertical direction as shown in dotted outline at 84b and, in this position, it functions as a tape reel lock. Crank handle or winding crank 84 pivots through arc 84c from a vertical position 84b shown in dashed outline to a horizontal position relative to longitudinal axis 32y. The use of spring-loaded anti-rotation arm 78 follows the sampling tape payout and will stop reel motion when the tape is fully extended. The anti-rotation arm prevents a bottoming out of tape payout and then, continues reel turning to re-wind the tape in the opposite direction. Winding crank 84 is coupled with reel 70 by means of bushing 84d (see FIG. 4, cover 16b is removed).

Member 24 which includes the tape wiper housing is positioned between main reel housing 16 and stub barrel connector 30 contains spring loaded tape wiper actuation knob 24a. When re-winding gauging tape 66 to its full stow position, it is recommended that a tape wiper be used.

Spring loaded anti-rotation arm 78 follows the sampling measuring or gauging tape payout, and will stop reel 70 motion when a tape is fully extended. Because of a lack of direct access to cargo container 12a, it is possible without notice for the tape to bottom out and then, by continued reel turning, to cause the tape to re-wind in the opposite direction.

Figure 2A:
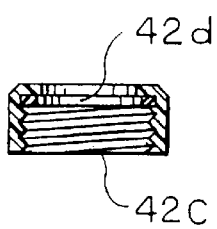
FIG. 2A is a sectional view of the cap sealing closure for the sample container of FIG. 2.

Sample bottle 42 as shown in FIG. 2 includes outer threads 42a to receive cap closure 42b, see FIG. 2A, provided with inner sealing threads 42c. After a sample has been placed into bottle 42, cap closure 42b, is placed onto the mouth of sample bottle 42 and inner sealing threads 42c mate with outer sealing threads 42a, and cap closure 42b is pressure tightened against sealing O-ring comprising elastomeric seal 42d and is locked into place onto bottle 42. Hand tightening of the cap closure 42b is all that is necessary. Vapor escape from the connected bottle is prevented by elastomeric sealing O-ring 42d.

Referring to FIG. 7, bottle fill attachment assembly 44 with connector 46 is connected to container 42 from outlet drain port 38 and fill tube connector 48d from cap 50 to sample flow control valve 48. Cap 50 includes entrance way 52 for receiving outlet tube or connector 48d. Connector 46 is connected to drain port 38 (see FIG. 1) for feeding a sample to bottle 42 through assembly 44. Coupling fill assembly 44 to sampling valve drain port 38 is accomplished by threading on connector 46 by eared coupling nut 46c to drain port fitting 38b of sampling valve 34. Normal hand tightening of this connection is sufficient for leak tight operation.

Bottle fill cap closure 50 includes seal plug bottle holder 50a coupled to retaining ring 50b. Cap closure 50 is partially cut away to show internal O-ring 50c, to prevent vapor escape, on an internal threaded part of the cap to provide a tight seal with complementary outer threads 42a (see FIG. 1) on outer rim of bottle 42.

Entrance way 52 is an opening for receiving fill tube connector 48d through seal plug 50a and exit way 54 is coupled with vapor return tube 54a and male connection fitting end 54b for connection with vapor return hose assembly 58, see FIG. 1.

Fill tube connector 48d is connected through sample flow control valve 48 to sleeve tube connector 46a for connection to outlet drain port 38. Coupling tube 46d is connected to bushing pipe 46e for connection with sleeve tube 46a. Coupling nut 46c is connected to an inlet side of in-line flow control valve 48 through pipe and bushing locking nut 48a and outlet side of control valve 48 is coupled through connector tube and locking nut 48b to fill tube connector 48d through coupler/decoupler 48c for rapid connection and disconnection with pipe or fill tube 48d.

In-line flow control valve 48 (see FIG. 7), is similar to sampling valve 34 in that each is of the type of a positive shut-off ball valve, requiring only a turn of handle 48e through 90° to open or to close.

Vapor return hose 60 is connected at connector end 60a to make connection end 54b of vapor return tube 54a extending out of container 42 through cap 50 to the sample fill attachment, and at the other end by means of connector 60b to vapor return hose quick connection fitting 26. Connector 60b depresses ball 26a, and thereby allows free gas or vapor flow between the fill attachment and the closed interior gauging housing 16.

Connector 60b must be fully and firmly seated to the check valve fitting 26 to ensure opening of the check valve.

Fitting 26 completes the means for completing the displaced collection bottle vapor path back into the closed system, thereby creating a pressure balance between container 42 and housing 16, and provides a completely closed pathway. Balancing of the vapor flow path established by the vapor return hose 60 provides for a safety feature such that an unwanted burst of product sample into the sample bottle does not occur.

Vapor control hose assembly 58 provides an important function of avoiding a negative pressure above the outgoing fluid collected from an atmospheric system so that flow is not diminished to a trickle. The condition is avoided since outgoing fluid will displace an equal volume of air being vented from the sample collection bottle via the vapor return hose, back into the closed system, thus maintaining the pressure balance within the system.

Pressure vacuum valve push button 20 is depressed to assure complete drainage of the extracted sample through push button valve 20a. Button 20 is not depressed during sample collection, but it can be optionally depressed when all of the product sample is thought to have been drained.

After all attachments between assembly 44 and port 38 are completed, unlock the tape and lower the tape for approximately three inches or until a stop can be felt due to a lack of pull on the tape. At this point, the product can be seen discharged from the product sampling tube through window 62 in FIG. 3D and (or the other side, window 62a, not shown), the product is observed as filling the opening.

Open sample flow control valve 34 by handle 36, as seen in FIG. 1, and product drainage can be viewed through window 62. Then open sample flow control valve 48 of bottle fill attachment assembly 33 by handle 48e to fill sample bottle 42. After a sample is taken, sample flow control valve 48 is closed. If no further samples are to be taken, sampling valve 34 may be returned to its open to tank position by handle 36, and closing off exit way to attachment assembly 44, at which position valve sample ports 38 and 38a are sealed off from container 12a. To insure full opening of the ball check valve at the bottom of the sample tube, the sampling valve ball has a built-in spring loaded pusher pin as disclosed in U.S. Pat. No. 5,452,620 which is released when the sampling valve is placed into its closed position. This feature insures free passage product sampling tube 33 through the valve.

The same procedure is also necessary even if one starts with a clean sample bottle 42. Flow control valve 48 is opened to allow a sample to fill bottle 42 and displace clean air in bottle 42; this preliminary procedure is necessary in order to avoid any vapor emission, and to empty sealed container 42, sampling barrel 32, housing 16 and product sampling tube 33.

The procedure for filling sample bottle 42 is as follows:

Both vapor control valve 12, and sampling valve 34 and sample flow control valve 48 are opened, then product sampling tube 33 and gauging tape 66 are lowered while allowing some dwell time, as indicated by the position shown in FIG. 3B with gauging tape 66 visible through window viewing port 62. Then product sampling tube 33 is steadily raised to its full stow position (see FIG. 3).

After visually confirming the full stow position at either the primary sight view port 22 or secondary sight port 22a, the tank's vapor control valve 12 is closed, thereby fluidly disconnecting housing 16 from the tank container 12a, and any internal tank pressure. Sampling valve 34 is then closed, and its spring loaded push button (see U.S. Pat. No. 5,452, 620) is permitted to rise to engage ball 33a.

Product sampling tube 33 is then lowered, and in doing so, pushes up its internal ball check valve, indicated by ball 33a, allowing a fluid product to flow out of the product sampling tube 33 into the interior vapor valve barrel 32 and into sampling valve 34 and through bottle fill attachment assembly 44 to bottle 42. Sample flow control valve 48 is then closed.

With vapor return hose 60 connected to vapor return check valve fitting 26, a pressure balance between the interior housing pressure and sample bottle is established. As the bottle is filling and thereby displacing the air/vapor mixture within it, a declining out balancing pressure is being maintained within the bottle. Therefore, a sudden burst of fluid or liquid into the sample bottle will not occur, and fluid or liquid flow will be mainly due to dimple gravity flow as the material flows downwardly.

Normally, with the minimum amount of pressure capacity trapped within the sampling assembly or system, at or near completion of bottle filling, little or no positive pressure remains trapped in the system. Before removing the filled sample bottle, close sampling valve 34 and disconnect vapor return hose assembly 58 from vapor return hose fitting 26.

The balancing vapor flow path established by the vapor return hose prevents an unwanted burst of product sample into the sample bottle.

Liquid which is now at the bottom of container tank 12a, can be compared to a metal can, with a mixture of air and product vapor above it. When sample flow control valve 48 is opened, product from tank 12a in product sampling tube 33 will begin to fill bottle 42, and at the same time, vapor return hose assembly 58 returns to the system the same amount of air displaced from sample bottle 42. If the same amount of air displaced from sample bottle 42 were not returned through, vapor return hose assembly 58, a negative pressure above the outgoing fluid would be developed. If this condition were allowed, product flow would soon diminish to a trickle.

What is claimed is:

1. A portable sampling system for use with a cargo tanks vapor control valve or other tank entry device to enable an operator to extract and bottle a product sample in place without transfer of the collected sample to another container thereby using the same container for both collection and bottling and without transfer of the collected sample through an open atmosphere, comprising:

a hand held gauging apparatus including a gauging tape;

a built-in sampling valve and sample bottle fill attachment assembly associated with said hand held gauging apparatus for collection of a product sample free of human contact with the product sample; and a vapor return hose assembly coupling said built-in sampling valve and bottle fill attachment assembly, to said hand held gauging apparatus to provide a balanced vapor flow path into a product sample container for eliminating vapor release to the atmosphere and prevent an unwanted burst of sample to protect an end user from, possible exposure to toxic vapors.

2. The system of claim 1, wherein said built-in sampling valve is operable in conjunction with and independently of the cargo tank's existing control valve.

3. The system of claim 1, wherein said hand held gauging apparatus includes a casing and at least one tape viewing port.

4. The system of claim 1, including:

means coupled with a product sample retrieval mechanism for lowering and raising said product sample retrieval mechanism into and out of the cargo tank and passing through said vapor control valve and said built-in sampling valve, said sample retrieval mechanism including a product sampling tube, and means for discharging the sample through said sampling valve into the product sample container.

5. The system of claim 4, wherein said sampling valve includes a drain port for connection to the product sample container through said fill attachment assembly, and a clean out port.

6. The system of claim 1, wherein said product sample container includes a cap closure having an entrance way and an exit way for removal of a collected sample, said flow control valve includes an outlet connected with said entrance way and said exit way being connected to said vapor return hose assembly.

7. The system of claim 1, wherein said gauging apparatus includes a tape reel for said gauging tape, and an anti-rotation arm for said tape reel.

8. The system of claim 1, including means for coupling said bottle fill attachment assembly and said sampling valve.

9. The system of claim 8, wherein said fill attachment assembly includes a connector for coupling and uncoupling said fill attachment assembly from a drain port associated with said sampling valve through which a sample is discharged into the product sample container.

10. The system of claim 1, wherein said gauging apparatus includes a tape reel housing containing a reel and tape mechanism coupled with a tape wiper assembly for passing the gauging tape through said tape wiper assembly for obtaining a sample of a fluid in the product sample container, said product sample container being a closed container, a product sampling tube connected with said tape beyond said tape wiper assembly, and at least one viewing port associated with said housing for providing an operator with an immediate sense as to whether the tape is being lowered or raised.

11. The system of claim 1, including sampling flow control means adapted to be coupled to a sample retrieval mechanism and said product sample container for transferring a sample of fluid obtained by said retrieval mechanism to said product container, said vapor return hose assembly including a vapor return hose for returning vapors transferred to the product sample container through said flow control means from said sample retrieval mechanism.

12. The system of claim 1, wherein said vapor return hose assembly includes a vapor return check valve fitting housing a spring loaded vapor return check valve.

13. The system of claim 1, wherein said vapor return hose assembly includes a vapor return hose is coupled with said built-in sampling valve adapted for connection with a cargo tank containing a fluid to be sampled.

14. A method for filling a product sample container while avoiding vapor emission in which a tape reel mechanism is connected with a sampling barrel assembly through which a product sampling tube connected with a tape reel is lowered into a liquid cargo from which a product sample is to be derived, a vapor control valve coupled with said sampling barrel assembly and a sampling valve coupled between said sampling barrel assembly and a container of the liquid cargo comprising the steps of:

opening the vapor control valve and the sampling valve;

lowering the product sampling tube by unreeling the sample tape coupled with the tape reel through the sampling valve into the cargo container through the vapor control valve;

withdrawing the product sampling tube and closing the vapor control valve thereby fluidly disconnecting the reel housing from the product tank and any internal tank pressure; and closing the sampling valve and discharging the fluid from the product sampling tube.

15. A portable sampling system for use with a cargo tank's vapor control valve or other tank entry device to enable an operator to extract and bottle a product sample in place without transfer of the collected sample to another container thereby using the same container for both collection and bottling and without transfer of the collected sample through an open atmosphere, comprising:

a hand held gauging apparatus including a gauging tape;

a built-in sampling valve and sample bottle fill attachment assembly associated with said hand held gauging apparatus for collection of a product sample free of human contact with the product sample;

a vapor return hose assembly coupling said built-in sampling valve and bottle fill attachment assembly, to said hand held gauging apparatus for eliminating vapor release to the atmosphere and to protect an end user from, possible exposure to toxic vapors; and a sampling barrel connected with said hand held gauging apparatus, and a product sampling tube contained within said sampling barrel, said product sampling tube being adapted to pass through said sampling valve forming part of said sampling valve and bottle fill attachment assembly.

16. The system of claim 15, wherein said sampling barrel is provided with at least one viewing port.

17. A portable sampling system for use with a cargo tank's vapor control valve or other tank entry device to enable an operator to extract and bottle a product sample in place without transfer of the collected sample to another container thereby using the same container for both collection and bottling and without transfer of the collected sample through an open atmosphere, comprising:

a hand held gauging apparatus including a gauging tape;

a built-in sampling valve and sample bottle fill attachment assembly associated with said hand held gauging apparatus for collection of a product sample free of human contact with the product sample;

a vapor return hose assembly coupling said built-in sampling valve and bottle fill attachment assembly, to said hand held gauging apparatus for eliminating vapor release to the atmosphere and to protect an end user from, possible exposure to toxic vapors, said vapor return hose assembly being connected with a tape wiper assembly coupled with a retrieval mechanism through a vapor return check valve, said vapor return hose assembly being associated with a product sample retrieval mechanism; and a product container associated with said product sample retrieval mechanism and coupled with said vapor return hose assembly.

18. A portable sampling system for use with a cargo tank's vapor control valve or other tank entry device to enable an operator to extract and bottle a product sample in place without transfer of the collected sample to another container thereby using the same container for both collection and bottling and without transfer of the collected sample through an open atmosphere, comprising:

a hand held gauging apparatus including a gauging tape;

a built-in sampling valve and sample bottle fill attachment assembly associated with said hand held gauging apparatus for collection of a product sample free of human contact with the product sample;

a vapor return hose assembly coupling said built-in sampling valve and bottle fill attachment assembly, to said hand held gauging apparatus for eliminating vapor release to the atmosphere and to protect an end user from, possible exposure to toxic vapors; and a sampling barrel associated with a sample tube lowering means connected with said sampling valve, said sampling barrel including means for viewing the contents of said sampling barrel.

19. A portable sampling system for use with a cargo tank's vapor control valve or other tank entry device to enable an operator to extract and bottle a product sample in place without transfer of the collected sample to another container thereby using the same container for both collection and bottling and without transfer of the collected sample through an open atmosphere, comprising:

a hand held gauging apparatus including a gauging tape;

a built-in sampling valve and sample bottle fill attachment assembly associated with said hand held gauging apparatus for collection of a product sample free of human contact with the product sample;

a vapor return hose assembly coupling said built-in sampling valve and bottle fill attachment assembly, to said hand held gauging apparatus for eliminating vapor release to the atmosphere and to protect an end user from, possible exposure to toxic vapors;

said gauging apparatus including a tape reel housing containing a reel and tape mechanism coupled with a tape wiper assembly for passing the gauging tape through said tape wiper assembly for obtaining a sample of a fluid in a closed container, said product sample container being a closed container, a product sampling tube connected with said tape beyond said tape wiper assembly, at least one viewing port associated with said housing for providing an operator with an immediate sense as to whether the tape is being lowered or raised.

20. A portable sampling system for use with a cargo tank's vapor control valve or other tank entry device to enable an operator to extract and bottle a product sample in place without transfer of the collected sample to another container thereby using the same container for both collection and bottling and without transfer of the collected sample through an open atmosphere, comprising:

a hand held gauging apparatus including a gauging tape;

a built-in sampling valve and sample bottle fill attachment assembly associated with said hand held gauging apparatus for collection of a product sample free of human contact with the product sample;

a vapor return hose assembly coupling said built-in sampling valve and bottle fill attachment assembly, to said hand held gauging apparatus for eliminating vapor release to the atmosphere and to protect an end user from, possible exposure to toxic vapors;

sampling flow control means adapted to be coupled to a sample retrieval mechanism and a product sample container for transferring a sample of fluid obtained by said retrieval mechanism to said product sample container, said vapor return hose assembly including a vapor return hose for returning vapors transferred to the product sample container through said sampling flow control means from said sample retrieval mechanism; and said sample retrieval mechanism including a sampling barrel and a product sampling tube movable through said sampling barrel into a container containing a fluid to be sampled, said sampling barrel including at least one view port for viewing the interior of said sampling barrel, and a vapor valve securing collar for said sampling barrel.

21. A portable sampling system for use with a cargo tank's vapor control valve or other tank entry device to enable an operator to extract and bottle a product sample in place without transfer of the collected sample to another container thereby using the same container for both collection and bottling and without transfer of the collected sample through an open atmosphere, comprising:

a hand held gauging apparatus including a gauging tape;

a built-in sampling valve and sample bottle fill attachment assembly associated with said hand held gauging apparatus for collection of a product sample free of human contact with the product sample;

a vapor return hose assembly coupling said built-in sampling valve and bottle fill attachment assembly, to said hand held gauging apparatus for eliminating vapor release to the atmosphere and to protect an end user from, possible exposure to toxic vapors; and a product container being provided with a cap closure for closing off the contents and a cap closure mechanism having an entrance way and an exit way, said entrance way being coupled with a sample retrieval mechanism, and said exit way being coupled with a tape wiper assembly through said vapor return hose assembly to provide for a balanced vapor flow path so that an unwanted burst of product sample into the product container does not occur, and further so that a partial vacuum is not created within said enclosure during the draining of a collected product sample.

* * * * *